United States Patent
Petty

(10) Patent No.: US 9,708,933 B2
(45) Date of Patent: Jul. 18, 2017

(54) PLUG ASSEMBLY WITH RETAINING ELEMENT

(71) Applicant: UNITED TECHNOLOGIES CORPORATION, Farmington, CT (US)

(72) Inventor: Dale William Petty, Wallingford, CT (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 131 days.

(21) Appl. No.: 14/707,811

(22) Filed: May 8, 2015

(65) Prior Publication Data

US 2015/0354409 A1   Dec. 10, 2015

Related U.S. Application Data

(60) Provisional application No. 62/008,445, filed on Jun. 5, 2014.

(51) Int. Cl.

| F16B 39/10 | (2006.01) |
|---|---|
| F01D 25/24 | (2006.01) |
| F16B 39/32 | (2006.01) |
| G01N 21/954 | (2006.01) |
| F01D 9/06 | (2006.01) |

(52) U.S. Cl.
CPC .............. *F01D 25/24* (2013.01); *F16B 39/32* (2013.01); *F01D 9/065* (2013.01); *F05D 2220/32* (2013.01); *F05D 2260/31* (2013.01); *F05D 2260/83* (2013.01); *G01N 21/954* (2013.01)

(58) Field of Classification Search
CPC ... F01D 25/24; F05D 2260/36; F05D 2260/31
USPC .................................................. 411/119–121
See application file for complete search history.

(56) References Cited

U.S. PATENT DOCUMENTS

| 3,362,160 | A | * | 1/1968 | Bourgeois | F01D 21/003 415/118 |
|---|---|---|---|---|---|
| 5,639,113 | A | * | 6/1997 | Goss | B60R 21/2035 280/728.2 |
| 5,867,976 | A | * | 2/1999 | Ziegler, Jr. | F01D 21/003 415/118 |
| 5,882,044 | A | * | 3/1999 | Sloane | F16L 19/005 285/148.19 |
| 5,930,879 | A | * | 8/1999 | Piotrowski | B23P 19/08 29/227 |
| 6,322,306 | B1 | * | 11/2001 | Dutton | F16B 2/245 411/120 |
| 7,156,424 | B2 | * | 1/2007 | McCord | F16L 19/005 285/319 |
| 7,438,579 | B1 | * | 10/2008 | Pellen | H01R 13/622 439/312 |
| 7,600,789 | B2 | * | 10/2009 | Vyse | F16L 19/005 285/305 |

(Continued)

*Primary Examiner* — Gary Estremsky
(74) *Attorney, Agent, or Firm* — Cantor Colburn LLP

(57) ABSTRACT

The present disclosure relates to plug assemblies within a gas turbine engine. In one embodiment, a plug assembly includes a boss which includes a shaft and a collar, a retaining element including at least two prongs, and a plug including a shank and at least one retaining feature. The at least two prongs of the retaining element are configured to retain the plug to the boss.

16 Claims, 6 Drawing Sheets

(56) References Cited

U.S. PATENT DOCUMENTS

| | | | | |
|---|---|---|---|---|
| 8,555,765 B2* | 10/2013 | Graham, II | ............ | F41A 21/325 285/92 |
| 2006/0281595 A1* | 12/2006 | Narita | ................... | F16H 7/0848 474/109 |
| 2013/0207381 A1* | 8/2013 | Morrison | ............ | F16L 37/0842 285/82 |

* cited by examiner

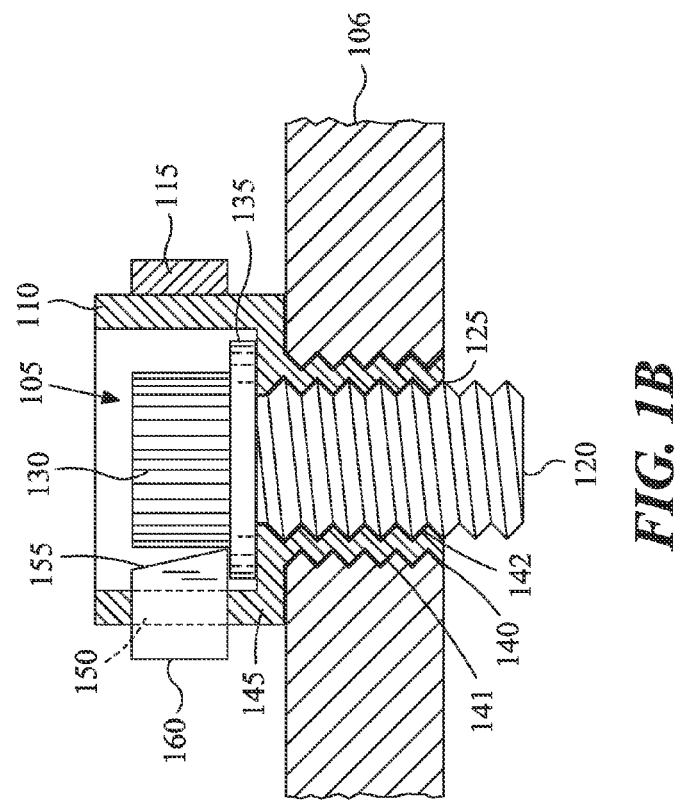
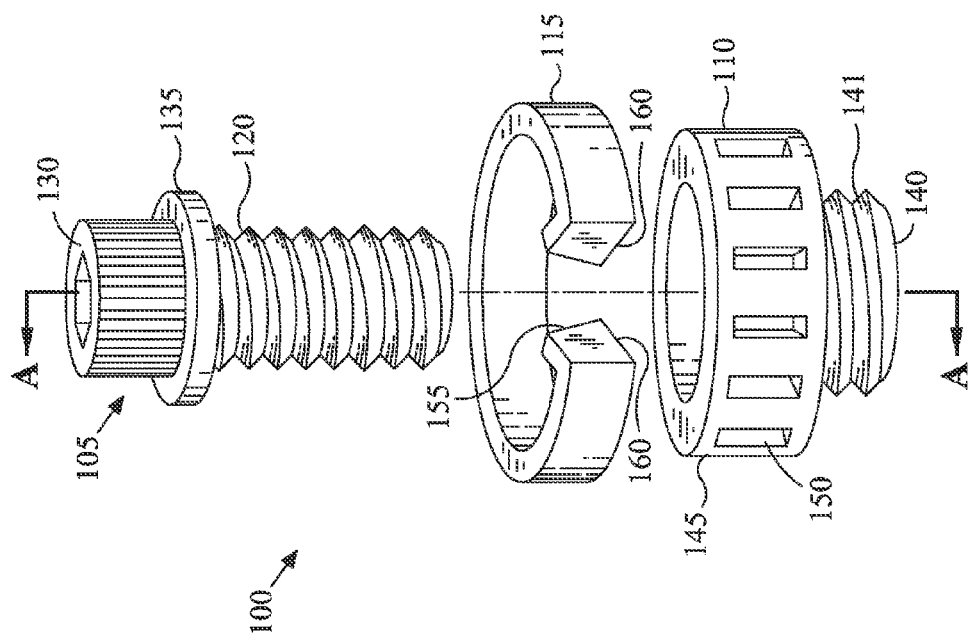

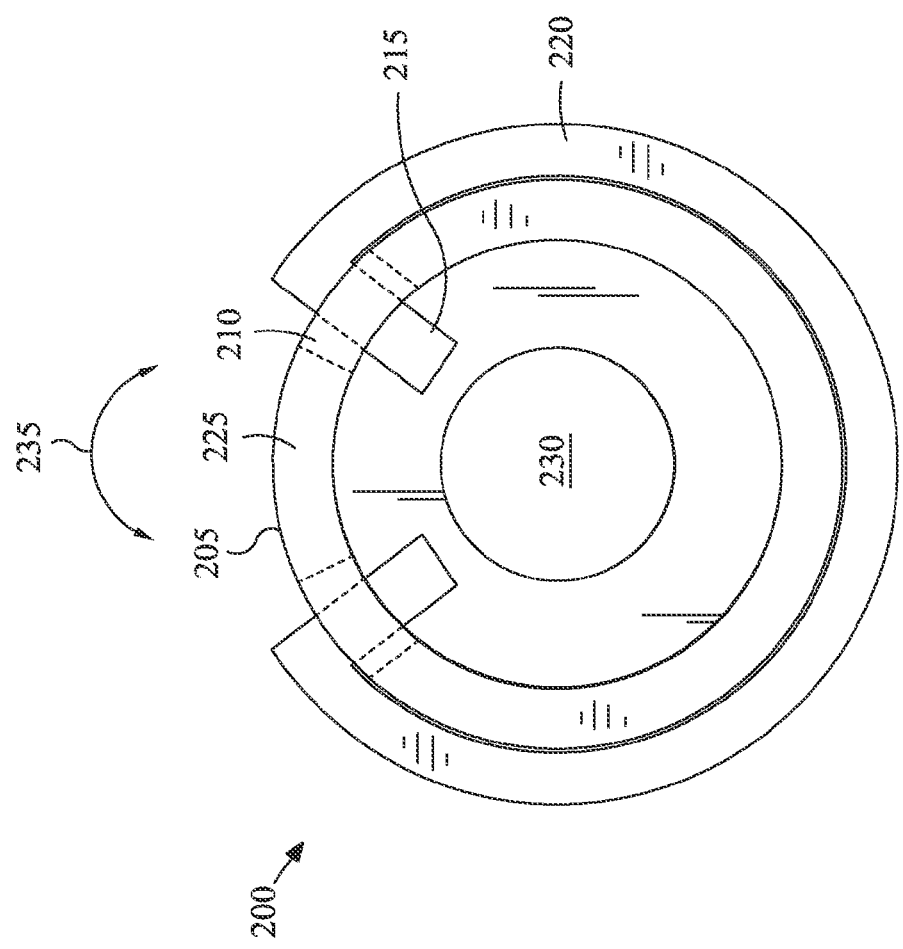

PLUG ASSEMBLY WITH RETAINING ELEMENT

CROSS-REFERENCE TO RELATED APPLICATIONS

This application claims priority to U.S. Provisional Application No. 62/008,445 filed on Jun. 5, 2014 and titled PLUG ASSEMBLY WITH RETAINING ELEMENT, the disclosure of which is hereby incorporated by reference in its entirety.

BACKGROUND

Gas turbine engines typically operate at high rotational speeds and high temperatures for increased performance and efficiency. In many cases, performance of an engine may be tied to proper operation and function of engine components. During operation, components may be damaged, fail or otherwise require maintenance. In addition, control of an engine may be based on the operation of components within an engine. Safety inspections and routine maintenance are often required to ensure safe operation and prevent engine failure. Many gas turbine engines include inspection ports to allow for inspection and/or maintenance of an engine. Conventional methods of sealing these ports are can be expensive and in some cases, may lead to foreign object damage (FOD) due to improper installation during manufacture or maintenance. Moreover, some gas turbine engines may have dozens of ports. In addition, correct operation and installation of port components may be required for safe and efficient operation of an engine. There is a need in the art for port components for gas turbine engines.

BRIEF SUMMARY OF THE EMBODIMENTS

Disclosed and claimed herein are plug assemblies for gas turbine engines including retaining elements. One embodiment is directed to a plug assembly including a boss which includes a shaft and a collar, and a retaining element including at least two prongs, wherein the retaining element is configured to engage with a portion of the collar. The plug assembly also includes a plug including a shank and at least one retaining feature, wherein the shank of the plug is configured to engage with the shaft of the boss, and wherein prongs of the retaining element are configured to releasably retain the at least one retaining feature of the plug to secure the plug to the boss.

In one embodiment, an outer surface of the shaft includes threads to engage the plug assembly with a port and a surface of the shaft in the axial cavity includes threads configured to retain the plug.

In one embodiment, the retaining element is at least one of a circlip and split ring.

In one embodiment, prongs of the retaining element are configured to engage with one or more openings in the collar.

In one embodiment, the retaining element is circumferentially coupled to one of an outer surface of the collar and an inner surface of the collar.

In one embodiment, the plug is at least one of a threaded plug, a plug having an extension, and a spring loaded plug.

In one embodiment, the at least one retaining feature of the plug is one of a castellation, gear, ridge and point of the plug.

In one embodiment, the plug includes a threaded shank configured to be releasably engaged with the shaft of the boss, the plug also includes a shoulder configured to engage with a seating shoulder of the boss.

In one embodiment, the retaining element is configured to prevent rotation of the plug by exerting force on the at least one plug feature.

In one embodiment, prongs of the retaining element include chamfered edges configured to engage with a socket and to expand the retaining element during insertion of the socket into the boss.

In one embodiment, the plug assembly is at least one of a boroscope plug assembly and inspection port assembly.

Another embodiment is directed to a plug assembly including a boss which includes a shaft and a collar, and a split ring retaining element including at least two prongs, wherein the split ring retaining element is configured to engage with at least a portion of the collar and the split ring retaining element is circumferentially coupled to the collar. The plug assembly also includes a plug including a shank and at least one retaining feature, wherein the shank of the plug is configured to engage with the shaft of the boss, and wherein prongs of the retaining element are configured to releasably retain the at least one retaining feature of the plug to prevent rotation of the plug when the prongs are engaged.

Other aspects, features, and techniques will be apparent to one skilled in the relevant art in view of the following detailed description of the embodiments.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein:

FIGS. 1A-1B depict graphical representations of a plug assembly according to one or more embodiments;

FIG. 2 depicts a planar representation of plug assembly elements according to one or more embodiments;

DETAILED DESCRIPTION OF THE EXEMPLARY EMBODIMENTS

Overview and Terminology

Figure 3:
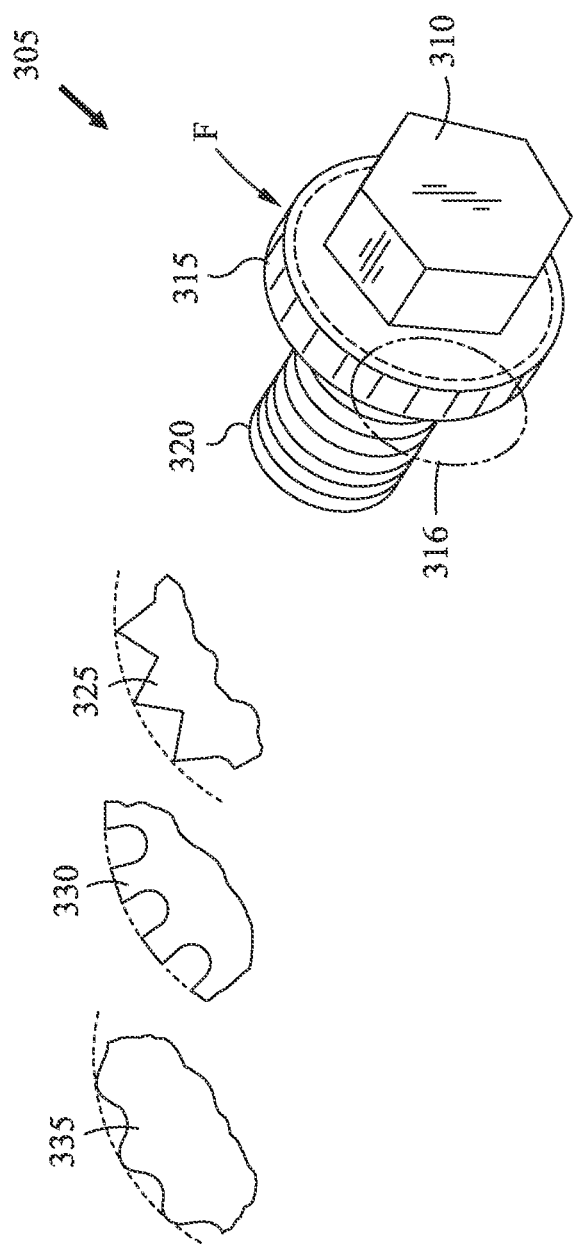
FIG. 3 depicts a graphical representation of a plug according to one or more embodiments.

One aspect of the disclosure relates to one or more components forming a plug assembly for a gas turbine engine, and in particular plug assemblies with retaining elements. In one embodiment, a plug assembly is provided for use with inspection ports into a gas turbine engine and/or for providing removable plugs to one or more ports in general. A plug assembly can include a boss, plug, and retaining element. The plug assembly may be secured to or integrally coupled with a port or opening of a casing, such as openings in one or more chambers of a gas turbine engine. In one embodiment, a retaining element is provided to releasably retain a plug and prevent the plug from being dislodged or removed from the plug assembly. This feature allows the inspection port to be protected while not in use and during vibrational stress.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment," "certain embodiments," "an embodiment," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics may be combined in any suitable manner on one or more embodiments without limitation.

Exemplary Embodiments

Referring now to the figures, FIGS. 1A-1B depict graphical representations of a plug assembly according to one or more embodiments. In FIG. 1A, an exploded view is depicted of plug assembly 100. According to one embodiment, plug assembly 100 includes boss 110, retaining element 115 and plug 105. Plug assembly 100 may be one or more of a boroscope plug assembly and inspection port assembly.

Boss 110 can include a shaft 140, a collar 145, and an axial cavity (shown in FIG. 2 as 230) to receive plug 105. As will be discussed in more detail below with FIG. 1B, boss 110 provides an interface for one or more port holes, such as port holes of a gas turbine engine casing. Boss 110 may be securely coupled or otherwise attached to an opening or port hole by one or more threaded, staking-in or integral formation with the port hole. In one embodiment, the inner and outer surfaces of shaft 140 can be threaded (e.g., include threads) as shown in more detail in FIG. 1B. The axial cavity of boss 110 can include internal threads to receive plug 105. A plug 105 includes shank 120, a head 130, and flange 135. Plug 105 can include at least one retaining feature as will be described in more detail below.

A retaining element 115 can be configured to exert a force on plug 105 and/or boss 110 to retain plug 105. In one embodiment, retaining element 115 is a split ring retaining element (e.g., circlip, etc.) having at least two prongs, shown as 160. Prongs 160 may include chamfered edges or ramped angles 155. In certain embodiments, retaining element 115 may include a single prong (not shown in FIG. 1A). Retaining element 115 is configured to engage with at least a portion of the collar 145. By way of example, retaining element 115 may be circumferentially located around the outer or inner portion of collar 145. According to one embodiment, plug 105, boss 110 and retaining element 115 may each be formed of the same material (e.g., metal alloy, etc.) as the casing or structure to which plug assembly 100 is mounted to.

According to one embodiment, collar 145 includes one or more openings, such as opening 150. Opening 150 may be shaped similar to prongs 160 in both proportion and appearance to receive prongs 160. Openings 150 may be configured to receive at least two of prongs 160 and may also be configured to allow for prongs 160 to engage with one or more features of plug 105.

FIG. 1B depicts a cross sectional representation of a plug assembly 100 of FIG. 1A along line A-A when inserted into port hole 106. Port hole 106 may be for one or more of a casing or wall of a gas turbine engine. According to one embodiment, boss 110 may be threaded to port hole 106. As shown in FIG. 1B, boss 110 includes threads 141 (e.g., outer shaft threads) to thread the boss to port hole 106 and threads 142 (e.g., inner shaft threads) to thread plug 105 to 110. Boss 110 may additionally include one or more securing connections (e.g., stake-in, welds, etc.) to couple boss 110 to port hole 106.

A plug 105 includes a threaded shank 120, threads shown as 125, a head 130, a flange 135, and at least one retaining feature. Plug 105 may be one or more of a threaded plug, a plug having an extension, and a spring loaded plug. Shank 120 may be partially or fully threaded and may include one or more grip portions (e.g., non-threaded portions). The head 130 may be one of a plurality of geometric configurations and can include points (e.g., hex—6-point head configuration). The geometric configuration may be at least one but not limited to hex, hex washer, slotted hex washer, or socket cap. Flange 135 is configured to rest on a shoulder flange of boss 110. Flange 135 may include one or more retaining elements. Plug 105 can be coupled to boss 110 when plug assembly 100 is secured to port 106, and is secured by retaining element 115 to prevent rotation of plug 105 from being dislodged from boss 110.

In FIG. 1B, retaining element 115 is circumferentially coupled to the outer surface of the collar 145 of the boss 110. Prongs 160 of retaining element 115 can prevent flange 135 from moving upward (e.g., out of the axial cavity of boss 110). Prongs may be secured by openings 150 in the collar 145 to secure retaining element 115. Prongs 160 can protrude through boss openings 150 to engage with the head, flange and/or retaining elements of plug 105. The retaining element 115 is also configured to prevent rotation of the plug 105 by exerting a force on at least one feature (e.g., head 130, retaining elements, etc.) of the plug.

A plug 105 is also shown and includes a shank 120 having threads 125. Shank 120 is configured to releasably engage with the shaft 140 (e.g., threads 141-142) such that head 130 may be rotated to tighten or loosen plug 105 from boss 110. Flange 135 may be flush with a seating shoulder of boss 110.

FIG. 2 depicts a top-down graphical representation of elements of a plug assembly according to one or more embodiments. Plug assembly 200 may be the plug assembly of FIGS. 1A-1B. Plug assembly 200 includes a boss 205 and retaining element 220 (plug is not shown in FIG. 2). Boss 205 of plug assembly 200 includes a collar 225 and a least one or more openings 210 in the collar. At the base of the collar 225 is the axial cavity 230 of the boss shaft (e.g., shaft 140). Retaining element 220 is circumferentially coupled to the outer surface of the collar 225. As such, the retaining element 220 surrounds collar 225. The retaining element 220 includes at least two prongs 215. The retaining element 220 is configured to engage with at least a portion of the collar 225, shown by prongs 215 extending into openings 210 in collar 225. As such, prongs 215 protrude through openings 210 to the interior of the collar 225. According to one embodiment, prongs 215 of retaining element 220 may extend outwardly, as shown by direction 235 to allow for insertion and removal of a plug (e.g., plug 105) into boss 205.

FIG. 3 depicts a graphical representation of a plug according to one or more embodiments. As shown, a plug 305 (e.g., plug 105) includes a head 310, a flange 315, and threaded shank 320. According to one embodiment, plug 305 includes at least one retaining feature. According to another embodiment, retaining features of the plug 305 on the outer perimeter of flange 315, such as an outer surface and/or on upper surface of flange 315. Exemplary region 316 as shown in FIG. 3 may include at least one retaining feature, such as at least one of a gear 325, castellation 330, ridge 335. Retaining features of the plug 305 can engaged with retaining element prongs to prevent rotation of the plug 305 while engaged within the boss of a plug assembly. According to one embodiment, a retaining element can prevent rotation of the plug 305 by exerting a force on a gear 325, castellation 330, ridge 335. Retaining features such as the gear 325, castellation 330, ridge 335 can prevent rotation of a plug 305 of a gas turbine engine under vibrational stress.

Figure 4:
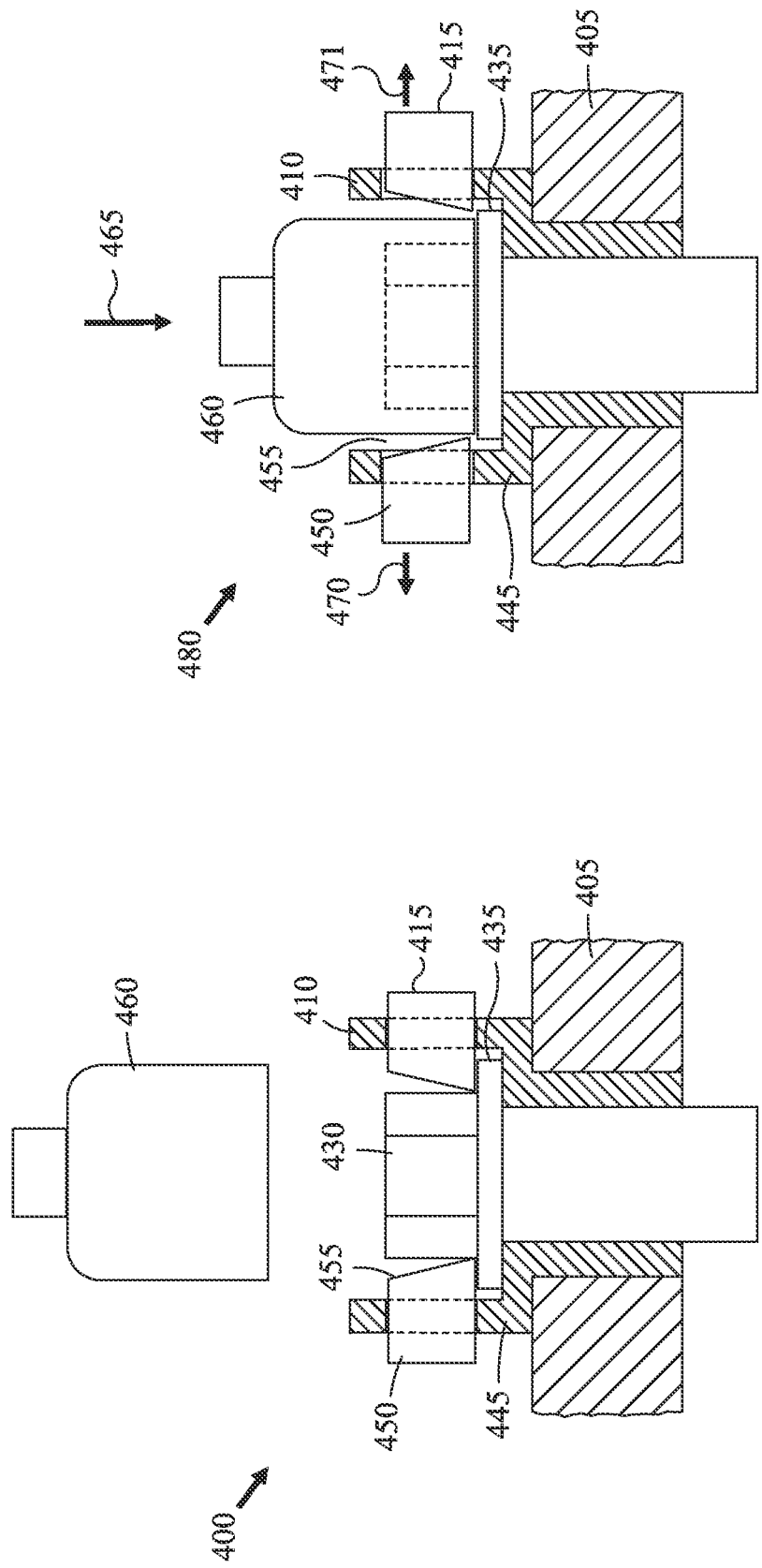
FIGS. 4A-4B depict graphical representations of a plug assembly according to one or more embodiments.

FIGS. 4A-4B depict a graphical representation of a plug assembly including a releasably engaging retaining element according to one or more embodiments. FIG. 4A depicts a cross sectional representation of a plug assembly 400 including a boss 410, retaining element 415 and plug 430, with retaining element 415 engaged with plug 430. In FIGS. 4A-4B, plug assembly 400 is secured to port 405. When engaged, prongs 450 of retaining element 415 prevent rotation of the plug 430 by exerting a force on the at least one plug feature. Retaining element 415 is circumferentially engaged with collar 445 of boss 410. According to one embodiment, retaining element 415 is above flange 435 of plug 430.

According to one embodiment a tool, such as a socket, can remove plug 430 from boss 410. FIG. 4A depicts socket 460 not engaged with the plug assembly 400. In FIG. 4B, tool 460 is shown engaged with plug assembly 400 for removal or insertion of plug 430 (not shown in FIG. 4B). Tool 460 is at least one of a fixed socket, interchangeable socket, ratcheting tool or non-ratcheting tool.

According to one embodiment, retaining element 415 may be configured to release from plug 430 upon insertion of tool 460 as shown by direction 465. In particular, prongs 450 of the retaining element 415 include chamfered edges 455 configured to engage with the tool 460 allows the plug to be inserted or removed from the boss 410 as prongs are moved outward as shown by directions 470 and 471.

Figure 5:
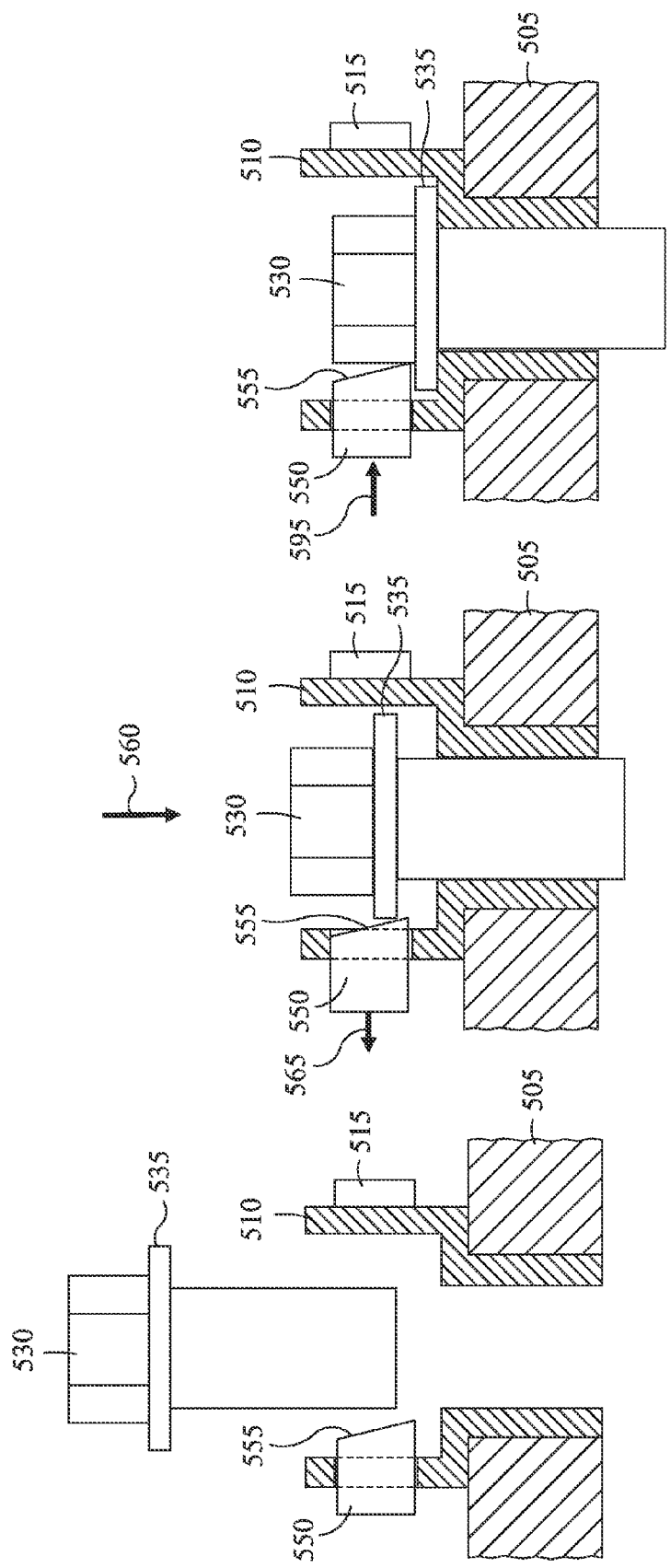
FIGS. 5A-5C depict a graphical representation of a plug assembly according to one or more embodiments.

FIGS. 5A-5C depict cross-sectional graphical representations of a plug assembly according to one or more embodiments. FIGS. 5A-5C depict port 505 including boss 510, retaining element 515 and plug 530. According to one embodiment, a retaining element 515 and a boss 510 allow for insertion and removal of a plug 530 without removal or insertion of retaining element 515. In that fashion, the retaining element 515 may releasably engage with the plug 530, but will not be fully removed from the plug assembly. By allowing the retaining element 515 to engage with the boss 510 during insertion and removal of plug 530, the risk of FOD (foreign object damage) may be reduced. FIG. 5A depicts a cross section graphical representation of a plug assembly 500 with a plug 530 not engaged with boss 510 or retaining element 515.

FIG. 5B depicts plug 530 being inserted into an axial cavity the boss 510. The prongs 550 of the retaining element 515 include chamfered edges 555 configured to engage with at least one of the plug 530 or flange 535 for expanding the retaining element 515 as shown by direction 565 during insertion. As such, when downward force 560 is applied by plug 530 and/or a tool, the plug 530 expands chamfered edges 555.

FIG. 5C depicts retaining element 515 engaging with plug 530. After the plug 530 is inserted (e.g., tightened) into boss 510, the retaining element 510, and in particular the prongs 550, engages as shown by direction 595. FIGS. 5A-5C depict insertion of a plug 530, however, removal of plug 530 may be similar. For example, a tool may expand chamfered edges 555 for removal of plug 530.

Figure 6:
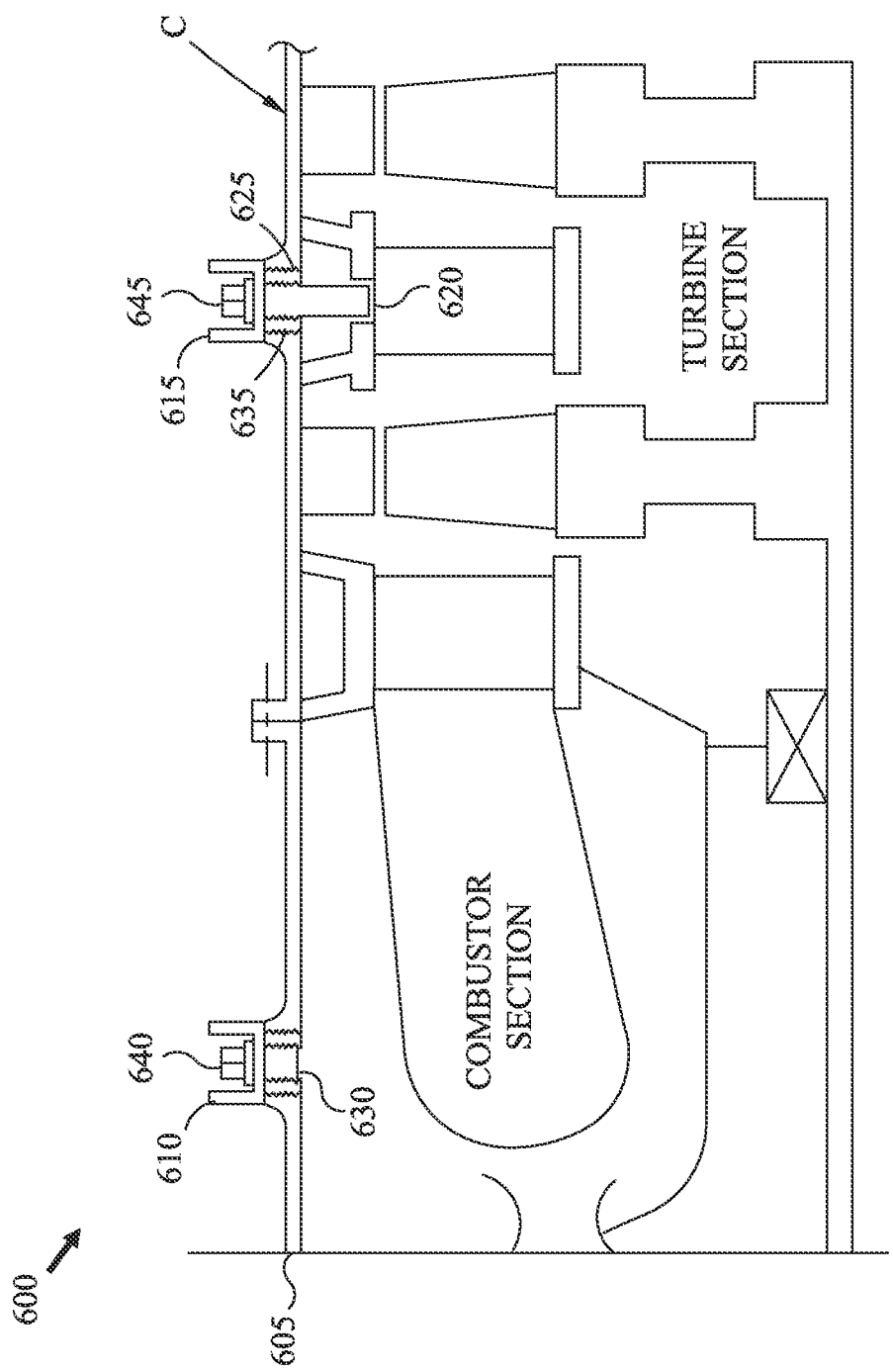
FIG. 6 depicts a graphical representation of a plug assembly within a gas turbine engine according to one or more embodiments.

FIG. 6 depicts a graphical representation of a plug assembly within a gas turbine engine according to one or more embodiments. Exemplary plug assemblies are shown as 610 and 615, which may be a boroscope plug assembly and inspection port assembly. Plug assemblies 610 and 615 are shown relative to ports 630 and 635, respectively, of casing 605. The plug assembly 610 includes plug 640 and plug assembly 615 includes plug 645.

In one embodiment, the plug 640 of the plug assembly 610 may be flush with the casing 605 or base structure of the gas turbine engine. Removal of the plug 640 from the plug assembly 610 allows inspection into the port 630 of the gas turbine engine. As such, the plug assembly 610 provides access to the inside of a structure of mechanical or other diagnostic reasons.

In another embodiment, a plug, such as plug 645 of the plug assembly 615, may have an extension 625 or be a spring loaded plug. The plug extension 625 or spring loaded plug may protrude past the interior casing 605 or base structure of the gas turbine engine. Also the plug extension 625 or spring loaded plug may be used to block a chamber 620 within the gas turbine engine. Blocking a chamber by a plug may be used to prevent the free flow of a medium within the chamber. Removal of the plug 645 from the plug assembly 615 allows inspection into the port 635 of the gas turbine engine. As such, the plug assembly 615 provides access to the inside of a structure or chamber for mechanical or other diagnostic reasons.

While this disclosure has been particularly shown and described with references to exemplary embodiments thereof, it will be understood by those skilled in the art that various changes in form and details may be made therein without departing from the scope of the claimed embodiments.

What is claimed is:

1. A plug assembly comprising:
 a boss including a shaft and a collar, wherein the shaft and collar include an axial cavity;
 a split-ring retaining element including at least two prongs, wherein the retaining element is configured to engage with at least a portion of the collar;
 a plug including a shank and at least one retaining feature, wherein the shank of the plug is configured to engage with the shaft of the boss, and wherein the at least two prongs of the retaining element are configured to releasably retain the at least one retaining feature of the plug securing the plug to the boss,
 wherein the at least two prongs extend toward a radial center of the split-ring retaining element and have radially inner facing portions with radially inner facing chamfered edges that ramp radially outwardly, towards an axial top thereof, and wherein an axial bottom of the at least two prongs is configured to engage an axial top of an annular flange of the plug.

2. The plug assembly of claim 1, wherein an outer surface of the shaft includes threads to engage the plug assembly with a port and a surface of the shaft in the axial cavity includes threads configured to retain the plug.

3. The plug assembly of claim 1, wherein the retaining element is circumferentially coupled to one of an outer surface of the collar and an inner surface of the collar.

4. The plug assembly of claim 1, wherein the plug is at least one of a threaded plug, a plug having an extension, and a spring loaded plug.

5. The plug assembly of claim 1, wherein the at least one retaining feature of the plug is one of a castellation, gear, ridge and point of the plug.

6. The plug assembly of claim 1, wherein the plug includes a threaded shank configured to be releasably engaged with the shaft of the boss, the plug also includes a shoulder configured to engage with a seating shoulder of the boss.

7. The plug assembly of claim 1, wherein the retaining element is configured to prevent rotation of the plug by exerting force on the at least one plug feature.

8. The plug assembly of claim 1, wherein the plug assembly is at least one of a boroscope plug assembly and inspection port assembly.

9. A plug assembly comprising:
a boss including a shaft on a bottom portion thereof and a collar on a top portion thereof, wherein the shaft and collar include an axial cavity;
a split ring retaining element including at least two prongs, wherein the split ring retaining element is configured to engage with at least a portion of the collar, and the split ring retaining element is circumferentially coupled to the collar;
a plug including a shank and at least one retaining feature, wherein the shank of the plug is configured to engage with the shaft of the boss, and wherein prongs of the retaining element are configured to releasably retain the at least one retaining feature of the plug to prevent rotation of the plug when the prongs are engaged,
wherein the at least two prongs extend toward a radial center of the split-ring retaining element and have radially inner facing portions with radially inner facing chamfered edges that ramp radially outwardly, towards an axial top thereof, and wherein an axial bottom of the at least two prongs is configured to engage an axial top of an annular flange of the plug.

10. The plug assembly of claim 9, wherein an outer surface of the shaft includes threads to engage the plug assembly with a port and a surface of the shaft in the axial cavity includes threads configured to retain the plug.

11. The plug assembly of claim 9, wherein the split ring retaining element is circumferentially coupled to one of outer surface of the collar and an inner surface of the collar.

12. The plug assembly of claim 9, wherein the plug is at least one of a threaded plug, a plug having an extension, and a spring loaded plug.

13. The plug assembly of claim 9, wherein the at least one retaining feature of the plug is one of a castellation, gear, ridge and point of the plug.

14. The plug assembly of claim 9, wherein the plug includes a threaded shank configured to be releasably engaged with the shaft of the boss, the plug also includes a shoulder configured to engage with a seating shoulder of the boss.

15. The plug assembly of claim 9, wherein plug assembly is at least one of a boroscope plug assembly and inspection port assembly.

16. A method of securing a plug to a threaded port hole, comprising:
threading a boss into the port hole;
inserting at least two prongs of a split-ring retaining element into respective openings in a collar of the boss;
wherein the at least two prongs extend toward a radial center of the split-ring retaining element and have radially inner facing portions with radially inner facing chamfered edges that ramp radially outwardly, towards an axial top thereof;
threading a plug into a threaded shaft in the boss, wherein a flange of the plug engages the radially inner facing chamfered edges of the at least two prongs, and downward force from the flange expands the chamfered edges by biasing the chamfered edges radially outwardly; and
axially securing the plug in the boss by threading the plug until the flange of the plug moves axially past the at least two prongs, the at least two prongs radially contract, and an axial bottom of the at least two prongs engages an axial top of the annular flange of the plug.

* * * * *